US008641781B1

(12) United States Patent
Miguelez et al.

(10) Patent No.: US 8,641,781 B1
(45) Date of Patent: Feb. 4, 2014

(54) SOCKET FOR PARTIAL HAND PROSTHESIS

(75) Inventors: John M. Miguelez, Palos Verdes Estates, CA (US); Robert Dodson, Grapevine, TX (US); Daniel Conyers, Beaverton, OR (US); MacJulian Lang, Portland, OR (US); Joseph Christopher Lake, Colleyville, TX (US)

(73) Assignee: Advanced Arm Dynamics of Texas Inc., Redondo Beach, CA (US)

( * ) Notice: Subject to any disclaimer, the term of this patent is extended or adjusted under 35 U.S.C. 154(b) by 124 days.

(21) Appl. No.: 13/041,354

(22) Filed: Mar. 5, 2011
(Under 37 CFR 1.47)

(51) Int. Cl.
*A61F 2/78* (2006.01)
*A61F 2/80* (2006.01)

(52) U.S. Cl.
USPC ............................................. 623/57; 602/21

(58) Field of Classification Search
USPC ..................................................... 623/57, 62
See application file for complete search history.

(56) References Cited

U.S. PATENT DOCUMENTS

| | | | | |
|---|---|---|---|---|
| 3,358,527 | A | * | 12/1967 | Lake et al. .................. 74/484 R |
| 4,685,929 | A | | 8/1987 | Monestier |
| 4,732,142 | A | * | 3/1988 | Hurlburt et al. ............... 606/237 |
| 5,413,611 | A | | 5/1995 | Haslam, II et al. |
| 5,568,957 | A | | 10/1996 | Haugs |
| 6,921,419 | B2 | | 7/2005 | Weir et al. |
| 7,273,463 | B2 | * | 9/2007 | Priore .............................. 602/21 |
| 7,867,287 | B2 | | 1/2011 | Puchhammer |
| 2006/0149180 | A1 | * | 7/2006 | Phelen ............................ 602/20 |
| 2009/0077706 | A1 | * | 3/2009 | Prather ................................ 2/21 |

OTHER PUBLICATIONS

Fairley, Miki, "State-of-the-Art: Upper-Limb Prosthetics Technology", The O&P EDGE, Oct. 2009, printed from http://www.oandp.com/articles/2009-10_01.asp on Feb. 25, 2011, 4 pages.
Lake, Chris, "Experience With Electric Prostheses for the Partial Hand Presentation: An Eight-Year Retrospective", Journal of Prothetics and Orthotics, Apr. 2009, vol. 21, No. 2, pp. 125-130.
Kurmala, Amitha, "Transforming Lives: The i-LIMB Prothetics System", Technizzel, Aug. 6, 2007, printed from http://technizzel.com/articles/materials-science/amithakurmala/transforming-lives-the-i-li . . . on Feb. 25, 2011, 3 pages.
"Scientists Unveil World's First Bionic Finger", Newslite, Dec. 9, 2009, printed from http://newslite.tv/2009/12/09/scientists-unveil-worlds-first.html on Feb. 25, 2011, 1 page.

(Continued)

*Primary Examiner* — Bruce E Snow
*Assistant Examiner* — Melissa Hoban
(74) *Attorney, Agent, or Firm* — K&L Gates LLP

(57) ABSTRACT

A socket is described for use with a partial prosthesis of the hand. The socket includes a base layer molded to encapsulate and conform to the contours of a natural hand. The base layer has a dorsal portion and a palmar portion. The palmar portion has a distal edge positioned, in use, proximal to the transverse metacarpal arch of a natural hand, and the dorsal portion having a distal edge positioned, in use, along a transverse span along a mid-portion of the dorsum of the natural hand in an area proximal to the area of the second through fifth metacarpals of a natural hand. The palmar portion of the base layer defines a first open area around the hypo-thenar eminence and a second open area surrounding on the palmar portion the thenar eminence and extending to the radial side of the second metacarpal on the dorsal portion.

21 Claims, 12 Drawing Sheets

(56) References Cited

OTHER PUBLICATIONS

Search Results for "Prepreg" printed from http://www.cascade-usa.com/products/FABRICATION/FABRICS%20-%20DACRON% . . . On Feb. 28, 2011, 1 page.

"Prepreg Carbon Fiber Products", Carbon Express, LLC, printed from http://mycarbonexpress.com/prepreg2.html on Feb. 28, 2011, 1 page.

"Directions for use of EPOX-ACRYL, Toughened Expoxide Polymer, UN 1066", publically available document accessed from internet on Feb. 2011, 2 pages.

Lake, Chris, "Experience with Electric Protheses for the Partial Hand Presentation", MEC Conferene, University of New Brunswick, Institute of Biomedical Engineeering, Frederiction, Canada, Aug. 14$^{th}$, 2008, 30 pages.

"The Electric Partial Hand Prothesis: A Nine Year Retrospective", ASSH/HT National Meeting (Combined Annual Meeting of the American Society for Surgery of the Hand (ASSH) and the American Society of Hand Therapists (ASHT), San Francisco California, Sep. 3-5, 2009. 65 pages.

* cited by examiner

SOCKET FOR PARTIAL HAND PROSTHESIS

BACKGROUND i. Field of the Invention

The invention relates to a socket for a partial hand prosthesis to which one or more prosthetic members, such as articulatable or nonarticulatable prosthetic finger prostheses, or tools for specific activities, may be attached.

ii. Description of the Related Art

When a person loses all or part of a hand due to an accident or a degenerative condition, or is born with a malformation of the hand, a full or partial prosthetic hand is used to assist the person with performance of daily activities. Designs for hand prostheses have evolved over many years of attempts to provide functional abilities that approximate those of a natural healthy hand. Exemplary prostheses are shown in U.S. Pat. No. 7,867,287 which describes a hand prosthesis which includes a chassis to which a number of finger prostheses are articulated. Fingers are actuated by a common drive housed within the chassis.

Partial hand losses where a portion of the natural hand remains require attachment of the prosthetic portion to the residual hand by means of an attachment device referred to as a socket. Previous partial hand socket designs have many variations and configurations. Prior designs encapsulate the entire residual hand and wrist to achieve the necessary suspension of the prosthetic members. A partial hand prosthesis sold commercially by Touch Bionics™ is a myoelectric prosthesis that has motor-powered fingers attached to a silicone skin. The silicone skin fits around a patient's residual hand and is connected to a wrist strap which provides the power source and communication links. Under the silicone skin there is a base layer that surrounds the residual hand from the metacarpophalangeal joint level proximally to below the wrist.

The foregoing discussion is intended only to illustrate various aspects of the related art in the field of the invention at the time, and should not be taken as a disavowal of claim scope.

SUMMARY

The socket design described herein is an improvement over the socket designs heretofore available for use with prosthetic devices for persons with amputations or malformations at the partial hand level. The design is particularly useful for amputations or losses of the hand wherein one to four fingers are removed, but at least portions of the proximal phalanx of the thumb and at least the body portions, and preferably all, of the metacarpals of the second through the fifth phalanges remain. Specific and defined areas of the hand anatomy are utilized to create an interface which provides stability with respect to the remaining hand anatomy, and good suspension of the prosthetic members attached thereto, without sacrificing the natural range of motion of the wrist and remaining thumb.

An embodiment of the socket for use with a partial hand prosthesis is described herein, wherein the natural hand has an ulnar side and a radial side and retains thenar and hypothenar eminences, at least the body portions of the metacarpals, and at least portions of the proximal phalanx of the thumb. Various embodiment of the socket include a base layer molded to encapsulate and conform to the contours of a natural hand, wherein the base layer has a dorsal portion and a palmar portion. The palmar portion in various embodiments has a distal edge positioned, in use, at or proximal to the transverse metacarpal arch of a natural hand. The dorsal portion in various embodiments has a distal edge positioned, in use, along a transverse span along a mid-portion of the dorsum of the natural hand in an area proximal to the area of the second through fifth metacarpal heads of a natural hand. The palmar and dorsal portions have a proximal edge configured for positioning, in use, distal to the heads of the radial and ulnar bones. Depending on the specific patient's soft tissue, the proximal edge of the palmar portion may be proximal to the carpal rows. In general, the proximal edge of the palmar portion is formed such that it will be positioned distal to the crease of the wrist. The positions of the proximal edges permit unhindered motion of the wrist when the socket is worn.

The palmar portion of the base layer defines a first open area around the hypothenar eminence and a second open area surrounding, on the palmar portion, the thenar eminence and extending around to the radial side of the second metacarpal on the dorsal portion.

The first arced portion joins the palmar and dorsal portions on the ulnar side, and the second arced portion joins the palmar and dorsal portions on the radial side.

The palmar portion includes a transverse distal band having a first section and a second section and an axial band having a distal end and a proximal end, with the distal end being joined to the transverse distal band. The transverse distal band is positioned, in use, along the transverse metacarpal arch of a natural hand. The distal edge is formed such that it will be positioned, in use, at or proximal to the transverse metacarpal arch. Various embodiments of the palmar portion also have a transverse proximal band joined to the proximal end of the axial band and extending laterally therefrom in one direction in a position opposite the first section of the transverse distal band. The transverse proximal band is preferably configured for positioning, in use, along a portion of the proximal transverse arch of the carpal rows distal to the wrist crease of the natural hand.

Various embodiments of the dorsal portion of the base layer include a transverse dorsal band contoured in use to span a mid-portion of the dorsum of the natural hand in an area, generally distal to the dorsal side of the wrist crease, and preferably, at or distal to the carpal rows, and more preferably, immediately distal to the distal carpal row. The dorsal band has a first end and a second end. In some embodiments, a dorsal axial band may be joined to and extend proximally from the second end of the transverse dorsal band. The first arced portion is preferably joined to the first end of the transverse dorsal band. The second arced portion is preferably joined to the second end of the transverse dorsal band and the second section of the transverse distal band. In various embodiments, the first section of the transverse distal band, the axial band, the transverse proximal band, and the first arced portion define the first open area, and the second section of the transverse distal band, the palmar axial band, and the radial side of the dorsal axial band define the second open area.

In certain embodiments, the socket may further include an outer layer joined to the base layer. The outer layer may be configured and contoured to substantially match the configuration and contours of the base layer. The outer layer may comprise an outer palmar portion, an outer dorsal portion, a first outer arced portion joining the outer palmar and outer dorsal portions on the ulnar side, and a second outer arced portion joining the outer palmar and outer dorsal portions on the radial side.

Various embodiments of the socket may additionally include a distal end cap joining at least a portion of the distal transverse dorsal band and a portion of the distal transverse palmar band. A fastening mount may be provided on the distal cap for releasably attaching at least one, and up to four prosthetic fingers.

In various embodiments, a fastening mount may be attached to the palmer portion for releasable locking attachment of a prosthetic member, such as a prosthetic tool for enabling the performance of an activity, such as sports equipment, entertainment devices, cooking tools, gardening tools, or small hand or power tools. A prosthetic tool may be mounted via a fastening mount to either the palmar or the dorsal portion of the socket, depending on the tool and its use.

Various embodiments of the socket may have a plurality of channels formed in one or both of the base layer and the outer layer for receiving signal transfer members, such as wires for electronic control of the prosthetic members. The fastening mount may have at least one port in communication with at least one channel for connecting the signal transfer members to the at least one prosthetic member.

The base layer and the outer layer may be releasably attached to each other or may be laminated together.

The socket may be formed from a polymer matrix composite selected from the group consisting of flexible or rigid thermoplastic resins and flexible or rigid thermoset resins. Alternatively, the socket may be formed from a pre-impregnated composite material.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DESCRIPTION

Figure 1:
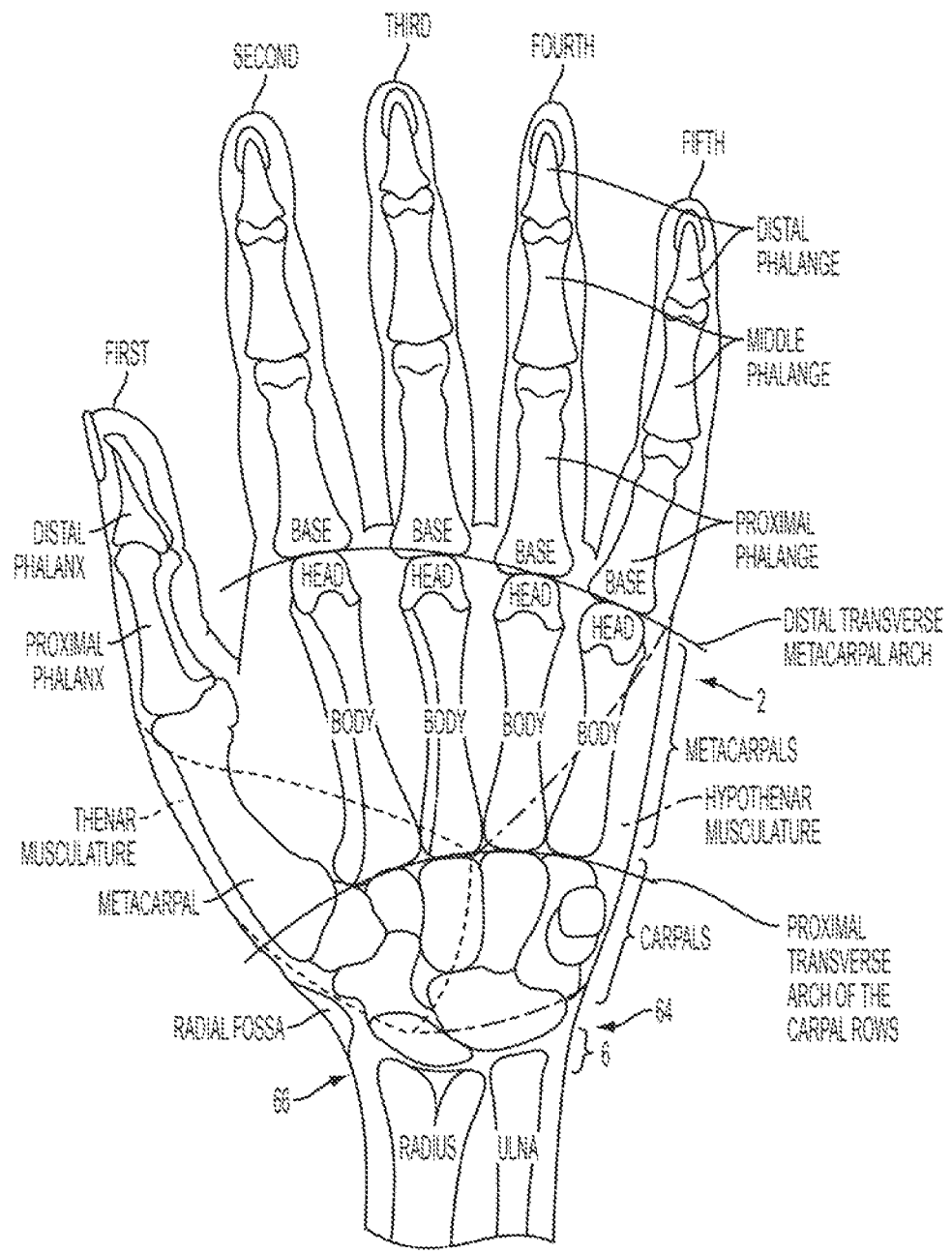
FIG. 1 is a palmar view of a portions of a human hand shown for anatomical reference herein.

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

In describing and claiming the present invention, the following terminology will be used in accordance with the definitions set out below.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to the position of the referenced area of the element discussed, such as a portion of the socket or hand, relative to the arm of the amputee or patient. For example, the fingers of the natural hand are distal to the wrist of the natural hand and the wrist is proximal to the fingers of the natural hand. The term "proximal" refers to the portion of the socket or hand closest to the patient's arm and the term "distal" refers to the portion of the socket or hand located farthest from the patient's arm. It will be further appreciated that for conciseness and clarity, spatial terms such as "vertical," "horizontal," "up," and "down" may be used herein with respect to the illustrated embodiments. However, prosthetic devices, such as the socket, and the hand and arms of a patient may be placed in many orientations and positions, and these terms are not intended to be limiting and absolute.

As used herein, terms such as "radial," "radial side," and the "radial direction" refer to the side on which the radial bone of the arm lies. As used herein, terms such as "ulnar," "ulnar side," and the "ulnar direction" refer to the side on which the ulnar bone of the arm lies. The thumb (or first digit or first phalange), for example, lies on the radial side and the little finger (or fifth digit or fifth phalange) lies on the ulnar side. The fingers from the index finger to the little finger (the second to the fifth digit or second to the fifth phalanges) proceed from the radial to the ulnar side.

As used herein, "transverse" with respect to a feature refers to the orientation of the feature in a direction extending between the radial and the ulnar sides, and the term "axial" with respect to a feature refers to the orientation of the feature in a direction extending between the distal and proximal directions. An "axial" direction generally lies along the longitudinal axis of the hand. Those skilled in the art will recognize, however, that the natural hand may not be symmetrical or have a straight longitudinal axis, and thus the longitudinal axis and the axial direction may be curved or angled, but will lie in the general direction of the long part of the natural hand in a direction between the distal and proximal directions.

As used herein "proximate to" with respect to the positioning or location of a feature relative to a natural body part means at or proximal to the natural body part. For example, if a feature of the socket or a feature of the layer of the socket described herein is positioned over an boney formation, it may be described as being positioned at the that location, whereas such a feature may also be positioned proximal to the boney formation. The exact position varies depending on the patient and the nature of the loss. Thus, a feature positioned in use proximate to a natural body part may be positioned at or proximal to that body part.

As used herein, "wrist crease" means the intersection between the arm and the natural hand where the soft tissue of the wrist creases when the hand or remaining portion of a hand is bent in any direction within its range of motion. Depending on the amount of soft tissue a patient has, the precise location of the wrist crease will vary. The socket of the present invention is designed to preserve the full range of natural motion of the wrist.

As used herein, the term "biocompatible" includes any material that is compatible with the living tissues and system(s) of a patient by not being substantially toxic or injurious and not known to cause immunological rejection. "Biocompatibility" includes the tendency of a material to be biocompatible.

Referring to FIG. 1, the palmar side of a natural hand 2 and wrist is shown. Various features of the natural hand 2 and wrist, such as the bones and general areas of the thenar and hypothenar musculature are shown for reference herein.

Several embodiments of the socket 10 are shown in FIGS. 2-12. The socket 10 includes generally a base layer 20 and an outer layer 70 (see FIG. 12). In the embodiment shown in FIGS. 2-5, the base layer 20 includes a palmar portion 12 and a dorsal portion 14. In the embodiment shown in FIGS. 6 and 7, the outer layer 70' is featured. The outer layer 70' includes an outer palmar portion 72', an outer dorsal portion 104', and an end cap 156' to which at least one, and up to four prosthetic fingers (not shown) may be releasably attached. Exemplary prosthetic members include prosthetic fingers or tools for specific activities. For example, the prosthetic member may be a tool for enabling the performance of an activity, such as a fishing rod or other light weight sports equipment, entertainment devices, such as music players, cooking tools, gardening tools, or small hand or power tools, such as hammers, screw drivers, or powered versions of hammers and drills.

Figure 2:
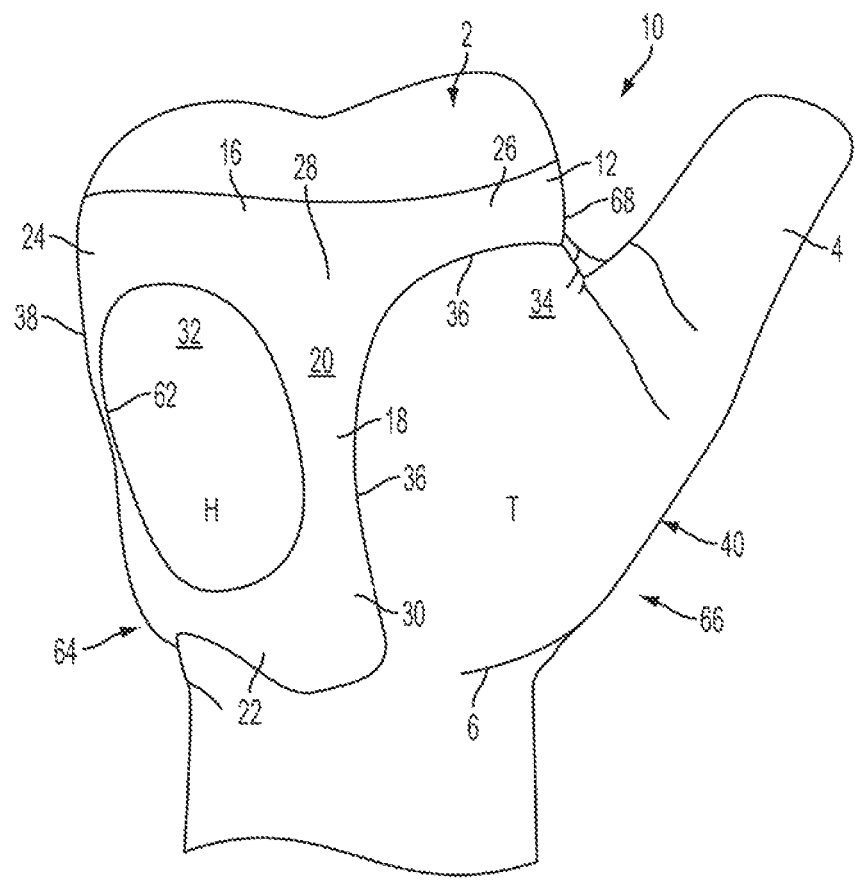
FIG. 2 is a palmar view of an embodiment of a contoured socket for a partial hand or finger prosthesis.

Referring to FIG. 2, the palmar portion 12 of base layer 20 includes a transverse distal band 16 having a first section 24 and a second section 26. The distal border of the palmar portion 12 of the socket 10 terminates proximate to, and preferably proximal to, the head of metacarpals 2-5 along the transverse arch, or if the head or heads of one or more metacarpals is missing distal border of the palmar portion 12 terminates just proximal to the most distal portion of the metacarpal. Thus, the distal band 16 is structured to be positioned in use generally at or proximal to (i.e., proximate to) the transverse metacarpal arch of a natural hand, in the general area as shown in FIG. 1. Those skilled in the art will recognize that the exact placement may vary depending on the nature and extent of the hand loss.

The palmar portion 12 shown in FIG. 2 also includes an axial band 18 having a distal end 28 and a proximal end 30. The distal end 28 of axial band 18 is joined to the transverse distal band 16. The palmar portion 12 also includes a transverse proximal band 22 joined to the proximal end 30 of the axial band 18 and extends laterally therefrom in the ulnar direction in a position generally opposite the first section 24 of the transverse distal band 16. In general, the proximal edge or border of the palmar portion 12 in the socket 10 design is formed such that it will be positioned distal to the crease 6 of the wrist, along the proximal transverse arch of the carpal rows, distal to the heads of the radial and ulnar bones. Special care is taken to avoid pressure over the pisiform bone. Thus, the transverse proximal band 22 is configured for positioning, in use, along a portion of the proximal transverse arch of the carpal rows distal to the wrist crease 6 of the natural hand 2. Depending on the specific patient's soft tissue, the proximal edge of the palmar portion may be proximal to the carpal rows. The positions of the proximal edges permit unhindered motion of the wrist when the socket is worn. The axial band 18 of the palmar portion 12 is contoured to touch, in use, the palm of the natural hand 2 along a position between the thenar and hypothenar eminences, T, H.

The palmar portion 12 includes a first opening 32 that exposes the hypo-thenar eminence H of the natural hand 2. The first section 24 of the transverse distal band 16, the axial band 18, and the transverse proximal band 22, together with a first arced portion 38 on the ulnar side 64 define the first opening 32. The second section 26 of the transverse distal band 16 and the axial band 18 define a perimeter 36 of a second opening 34 configured to expose the thenar eminence T and the area 40 of the radial side 66 of the wrist of the natural hand, along the first metacarpal shaft, e.g., the thumb 4.

The socket 10 is unique in its suspension method which does not require excessive encapsulation of anatomy, joint limiting straps, or joint mechanisms. Pressure is applied with the socket 10 to the region of the hand 2 and wrist anatomy distal to wrist crease 6 in order to suspend against axially directed forces. Overall suspension is enhanced by allowing both the thenar (T) and hypo-thenar (H) musculature to protrude through specific windows created by first and second openings 32 and 34, respectively, in the socket design. These two muscle groups are purposely not encapsulated within the socket. The first and second openings 32 and 34 also enhance stability, propreoception and reduce heat build up within the socket 10 by providing ventilation which significantly improves patient comfort. Stabilizing pressure is applied longitudinally along the palmar aspect of the shaft of the third and fourth metacarpal bones which couples with pressure spread evenly on the dorsum 50 of the hand 2.

Figure 3:
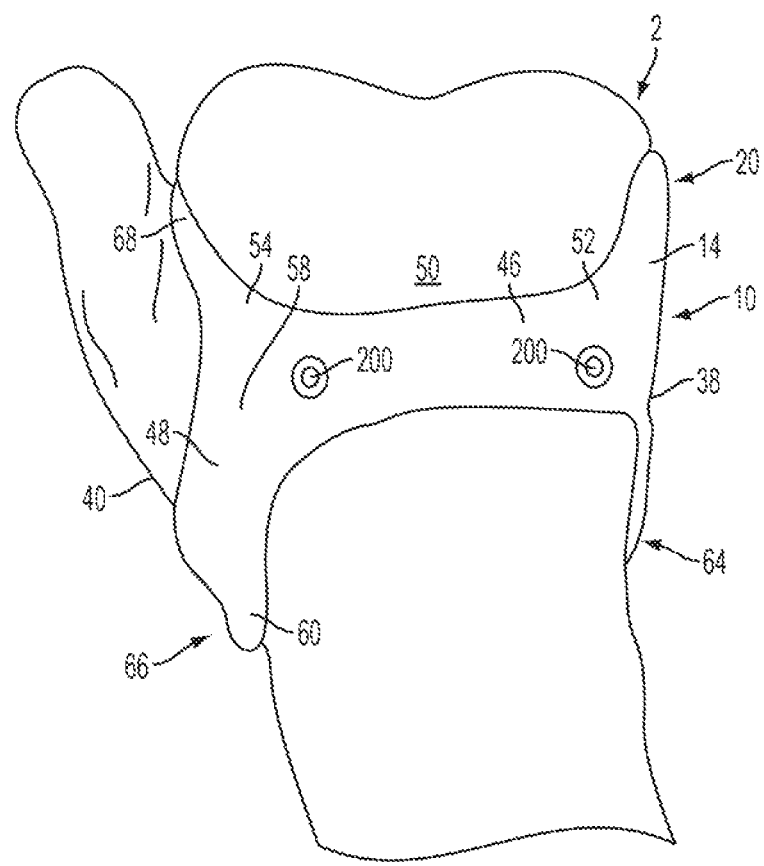
FIG. 3 is dorsal view of the embodiment of a contoured socket of FIG. 2.

Referring to FIG. 3, the proximal border of the dorsal portion 14 of the socket 10 initiates distal to the dorsal side of the wrist crease, and preferably immediately distal to the proximate transverse arch in the carpal rows, and contours around the soft tissue from medial to lateral to create a platform over the base of second through the fifth metacarpals. Thus, the dorsal portion 14 of the base layer 20 includes a transverse dorsal band 46 contoured in use to span a midportion of the dorsum 50 of the natural hand 2 in an area that initiates at the proximal border, as described above. The dorsal band 46 has a first end 52 and a second end 54. The position of the proximal border of the dorsal portion extends far enough in the proximal direction to provide support without restricting the full range of motion at the wrist and the first phalange. The positioning and the contoured fit aid in the suspension, stability, and propreoception of the socket 10 and the eventual prostheses through soft tissue expansion through the first and second hypo-thenar and thenar openings 32, 34. The open area also reduces heat build up within the socket 10 by providing ventilation which significantly improves patient comfort.

The distal border of the dorsal portion 14 of the socket 10 terminates proximal to the second through fifth metacarpal heads. The dorsal portion 14 of the socket 10 provides a counter pressure to the palmar portion 12 of the socket 10. Thus, the dorsal portion 14 shown in FIG. 3 includes a dorsal axial band 48 joined to and extending proximally from the second end 54 of the transverse dorsal band 46. The dorsal axial band 48 is configured so that in use so that it terminates at its proximal portion 60 at a location generally distal to the dorsal side of the wrist crease 6 of the natural hand 2, and preferably, at or distal to the carpal rows, and more preferably, immediately distal to the distal carpal row. The proximal portion 60 of the dorsal axial band 48 is contoured to conform to the natural hand 2 sufficiently to touch the natural hand, in use, and to avoid compression of the radial fossa. See FIG. 1.

Figure 4:
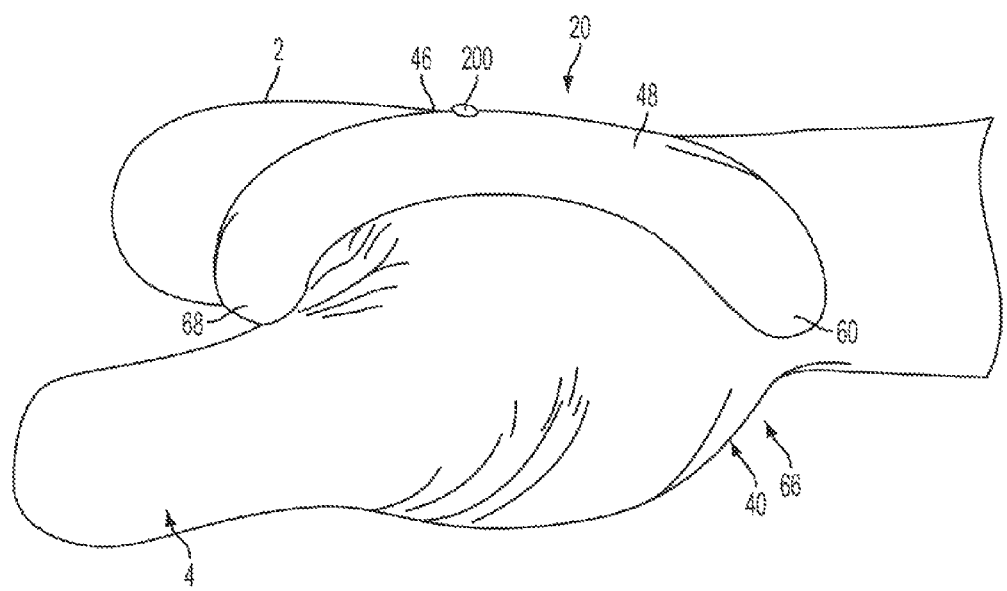
FIG. 4 is a lateral view from the radial side of the contoured socket of FIG. 2.

FIG. 4 shows the first arced portion 38. The first arced portion 38 is joined to the first end 52 of the transverse dorsal band 46, the first section 24 of the transverse distal band 16 and the transverse proximal band 22 of the palmar portion 12 to define a perimeter 62 of the first, or hypo-thenar opening 32. The first arced portion 38 on the radial side of the socket 10 allows for the longitudinal protrusion of the hypo-thenar musculature through the opening 32. The first arced portion 38 of the socket 10 is contoured to the radial side of the second metacarpal shaft around to the dorsum 50 of hand 2. Special care is taken to limit excessive pressure around the radial fossa. See FIG. 1.

Figure 5:
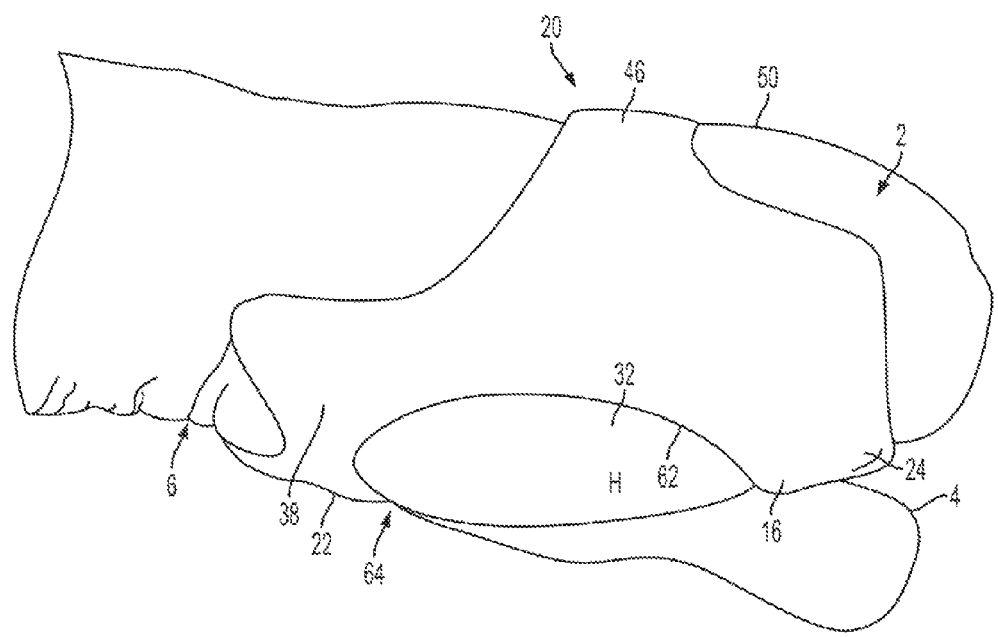
FIG. 5 is a lateral view from the ulnar side of the contoured socket of FIG. 2.

FIG. 5 shows the second arced portion 68 which is joined to the second end 54 of the transverse dorsal band 46 and the second section 26 of the transverse distal band 16. The second arced portion 68 of the socket 10 is contoured along the ulnar side 64 of the fifth metacarpal shaft just distal to the base and proximal to the metacarpal head. The first and second arced portions 38, 68 and the transverse distal and transverse dorsal bands 16, 46 are contoured to provide, in use, stabilizing pressure along the transverse metacarpal arch of a natural hand 2. The second opening 34 allows for protrusion of the oblique thenar musculature T along the thenar crease distally through the web space to the dorsum 50 of the hand 2.

Figure 6:
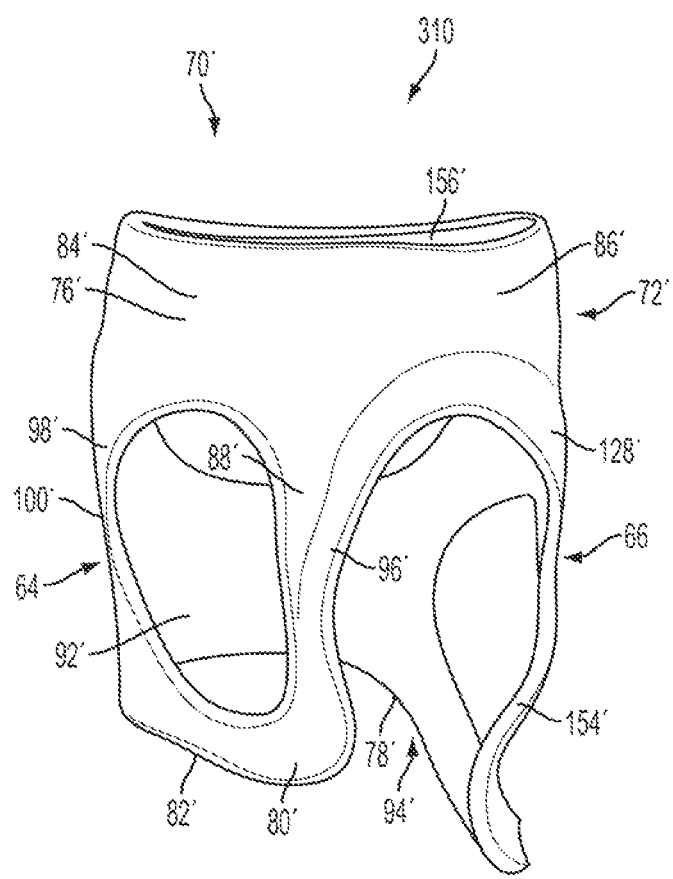
FIG. 6 is an alternative embodiment of the palmar view of a socket design for a partial hand or finger prosthesis showing the distal end cap.
Figure 7:
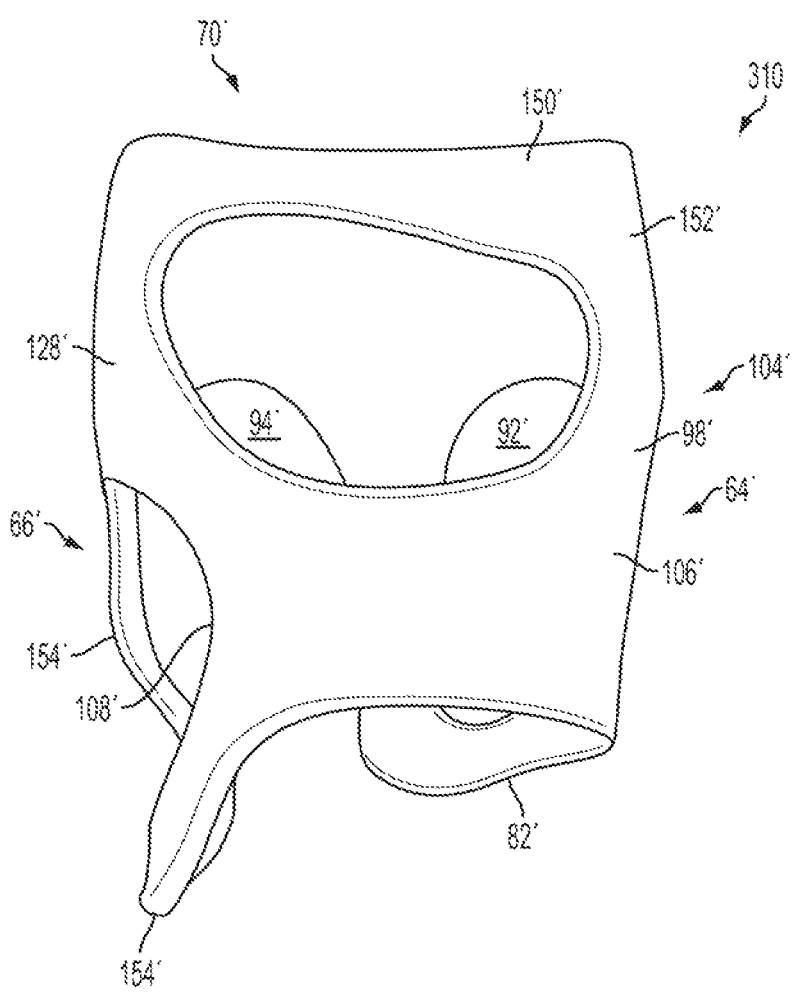
FIG. 7 is a dorsal view of the embodiment of the socket of FIG. 6.

FIGS. 6-7 show an alternative embodiment of the socket 310 design from the perspective of the outer layer 70'. The outer layer 70' is attached to a base layer, such as a layer 20 (see FIG. 12). Layer 20 is thinner than layer 70'. The base and outer layers are configured and contoured to substantially match each other. The base layer may extend slightly farther along the proximal and dorsal edges to provide comfort to the patient. The outer layer 70' includes generally an outer palmar portion 72', an outer dorsal portion 104', a first outer arced portion 98' joining the outer palmar and outer dorsal portions 72', 104' on the ulnar side 64, and a second outer arced portion 128' joining the outer palmar and outer dorsal portions 72', 104' on the radial side 66.

The outer palmar portion 72' shown in FIG. 6 includes an outer distal transverse palmar band 76' which has a first section 84' and a second section 86' and is positioned, in use, proximate to, and preferably proximal to, the transverse metacarpal arch of a natural hand 2.

FIG. 7 shows the outer dorsal portion 104' as including an outer proximal transverse dorsal band 106' contoured to span, in use, a mid-portion of the dorsum 50 of the natural hand 2 in an area distal to heads of the radial and ulnar bones, and depending on the soft tissue of the particular patient, proximal to the distal carpal rows, (See FIG. 1), but in general, distal to the dorsal side of the wrist crease 6. An outer distal transverse dorsal band 150' is contoured to span, in use, a distal portion of the dorsum 50 of the natural hand 2 in an area proximate to, and preferably proximal to, the transverse metacarpal arch of a natural hand 2. The outer proximal and distal transverse dorsal bands 106', 150' define a dorsal opening 152'. The outer dorsal layer 104' as shown also has an outer axial dorsal band 108' joined to and extending proximally from the outer proximal transverse dorsal band 106'. Also shown is an outer arced loop 154' positioned on the radial side 66. The loop 154' joins the outer axial dorsal band 108' to the second outer arced portion 128'.

Figure 8:
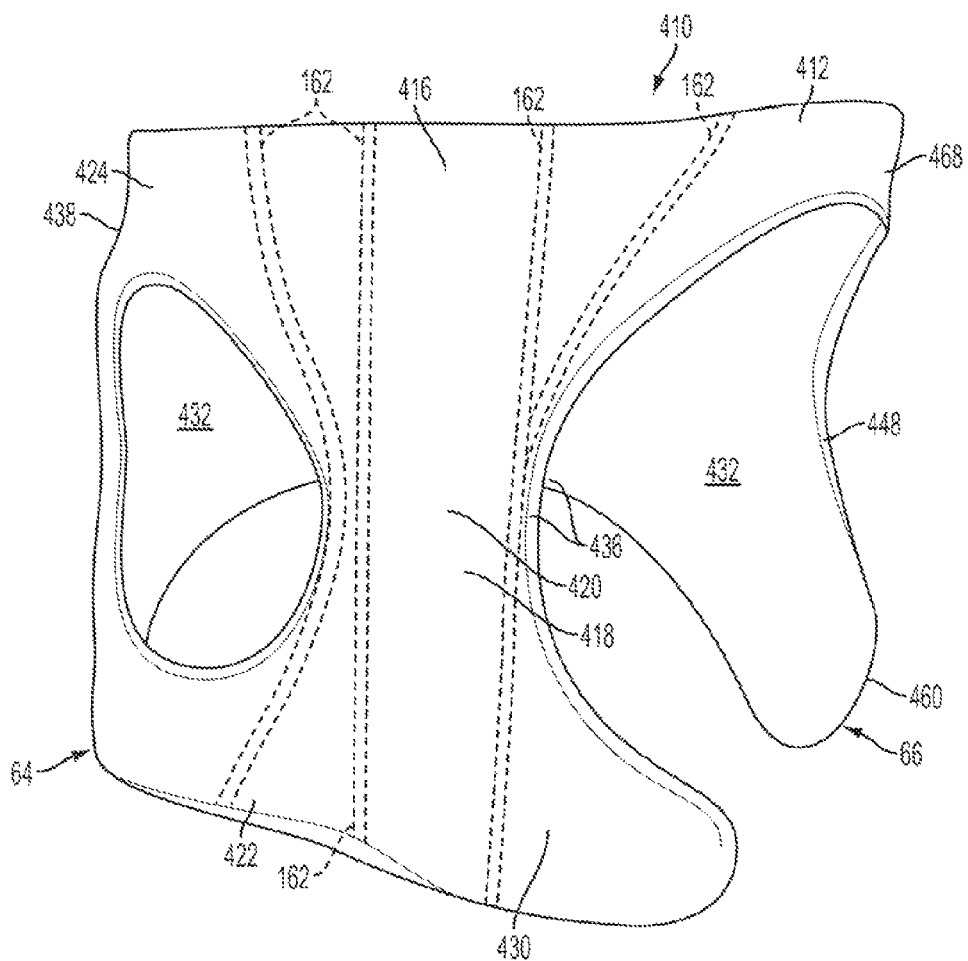
FIG. 8 is an alternative embodiment of the palmar view of a socket design for a partial hand or finger prosthesis, showing exemplary placement of channels for electrical signal connection in chain line.
Figure 9:
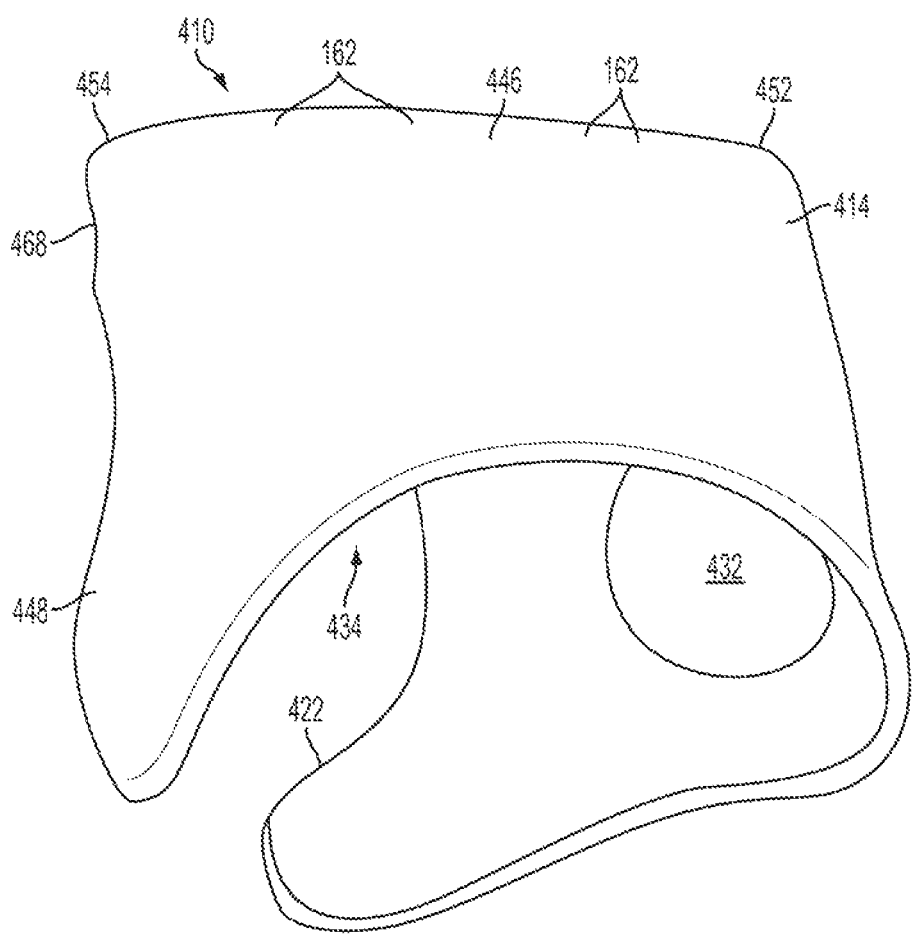
FIG. 9 is a dorsal view of the embodiment of the socket of FIG. 8 also showing exemplary placement of channels for electrical signal connection in chain line.
Figure 10:
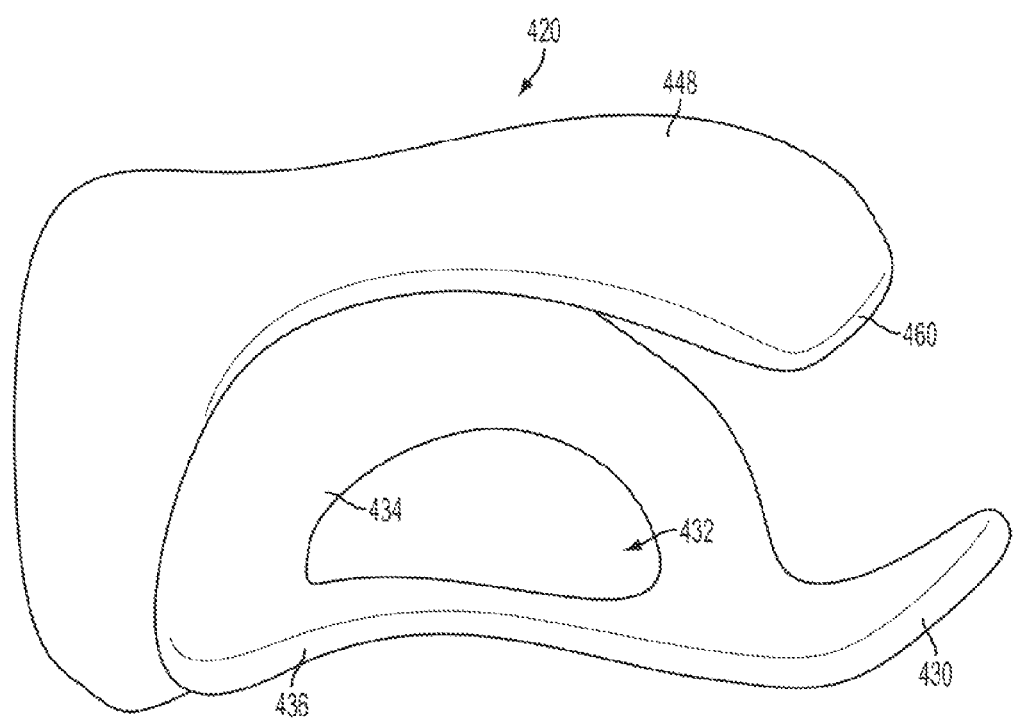
FIG. 10 is a lateral view from the radial side of the embodiment of the socket design of FIG. 8.

Another embodiment of the socket is shown in FIGS. 8-10. The socket 410, like the socket 10 and 310, includes a palmar portion 412 which includes a transverse distal band 416 having a first section 424 and a second section 426. The distal border of the palmar portion 412 of the socket 410 terminates proximate to, and preferably proximal to, the head of metacarpals 2-5 along the transverse arch, or if the head or heads of one or more metacarpals is missing distal border of the palmar portion 412 terminates just proximal to the most distal portion of the metacarpal. Thus, the distal band 416 is structured to be positioned in use generally at or proximal to (i.e., proximate to) the transverse metacarpal arch of a natural hand, in the general area as shown in FIG. 1. Those skilled in the art will recognize that the exact placement may vary depending on the nature and extent of the hand loss.

The palmar portion 412 shown in FIG. 8 also includes an axial band 418 having a distal end 428 and a proximal end 430. The distal end 428 of axial band 418 is joined to the transverse distal band 416. The palmar portion 412 also includes a transverse proximal band 422 joined to the proximal end 430 of the axial band 418 and extends laterally therefrom in the ulnar direction in a position generally opposite the first section 424 of the transverse distal band 416. In general, the proximal edge or border of the palmar portion 412 in the socket 410 design, like the proximal edge or border of the palmar portion 12 in the socket 10 design, is formed such that it will be positioned distal to the crease 6 of the wrist, along the proximal transverse arch of the carpal rows, distal to the heads of the radial and ulnar bones. As with the other embodiments of the socket design, special care is taken to avoid pressure over the pisiform bone. Thus, the transverse proximal band 422 is configured for positioning, in use, along a portion of the proximal transverse arch of the carpal rows distal to the wrist crease 6 of the natural hand 2. Depending on the specific patient's soft tissue, the proximal edge of the palmar portion may be proximal to the carpal rows. The positions of the proximal edges permit unhindered motion of the wrist when the socket is worn. The axial band 418 of the palmar portion 412 is contoured to touch, in use, the palm of the natural hand 2 along a position between the thenar and hypothenar eminences, T, H.

The palmar portion 412 includes a first opening 432 that exposes the hypo-thenar eminence H of the natural hand 2. The first section 424 of the transverse distal band 416, the axial band 418, and the transverse proximal band 422, together with a first arced portion 438 on the ulnar side 64 define the first opening 432. The second section 426 of the transverse distal band 416 and the axial band 418 define a perimeter 436 of a second opening 434 configured to expose the thenar eminence T and the area 440 of the radial side 66 of the wrist of the natural hand, along the first metacarpal shaft, e.g., the thumb 4.

The socket designs 10, 310, 410, are unique in their suspension method which does not require excessive encapsulation of anatomy, joint limiting straps, or joint mechanisms. Pressure is applied with the socket 10, 310 or 410 to the region of the hand 2 and wrist anatomy distal to wrist crease 6 in order to suspend against axially directed forces. Overall suspension is enhanced by allowing both the thenar (T) and hypo-thenar (H) musculature to protrude through specific windows created by first and second openings 32/32'/432 and 34/34'/434, respectively, in the socket design. These two muscle groups are purposely not encapsulated within the socket. The first and second openings also enhance stability, propreoception and reduce heat build up within the socket 10, 310, 410 by providing ventilation which significantly improves patient comfort. Stabilizing pressure is applied longitudinally along the palmar aspect of the shaft of the third and fourth metacarpal bones which couples with pressure spread evenly on the dorsum 50 of the hand 2.

Referring to FIG. 9, the proximal border of the dorsal portion 414 of the socket 410 initiates distal to the dorsal side of the wrist crease, and preferably immediately distal to the proximate transverse arch in the carpal rows, and contours around the soft tissue from medial to lateral to create a platform over the base of second through the fifth metacarpals. Thus, the dorsal portion 414 includes a transverse dorsal band 446 contoured in use to span a mid-portion of the dorsum 50 of the natural hand 2 in an area that initiates at the proximal border, as described above. The dorsal band 446 has a first end 452 and a second end 454. The position of the proximal border of the dorsal portion extends far enough in the proximal direction to provide support without restricting the full range of motion at the wrist and the first phalange. The positioning and the contoured fit aid in the suspension, stability, and propreoception of the socket 410 and the eventual prostheses through soft tissue expansion through the first and second hypo-thenar and thenar openings 432, 434. The open area also reduces heat build up within the socket 410 by providing ventilation which significantly improves patient comfort.

The distal border of the dorsal portion 414 of the socket 410 terminates proximal to the second through fifth metacarpal heads. The dorsal portion 414 of the socket 410, like that of the socket 10 and 310, provides a counter pressure to the palmar portion 412 of the socket 410. Thus, the dorsal portion 414 shown in FIG. 9 includes a dorsal axial band 448 joined to and extending proximally from the second end 454 of the transverse dorsal band 446. The dorsal axial band 448 is configured so that in use so that it terminates at its proximal portion 460 at a location generally distal to the dorsal side of the wrist crease 6 of the natural hand 2, and preferably, at or distal to the carpal rows, and more preferably, immediately distal to the distal carpal row. The proximal portion 460 of the dorsal axial band 448 is contoured to conform to the natural hand 2 sufficiently to touch the natural hand, in use, and to avoid compression of the radial fossa. See FIG. 1.

FIG. 10 shows the first arced portion 438 of socket design 410. The first arced portion 438 is joined to the first end 452 of the transverse dorsal band 446, the first section 424 of the transverse distal band 416 and the transverse proximal band 422 of the palmar portion 412 to define a perimeter 462 of the first, or hypo-thenar opening 432. The first arced portion 438 on the radial side of the socket 410 allows for the longitudinal protrusion of the hypo-thenar musculature through the opening 432. The first arced portion 438 of the socket 410 is contoured to the radial side of the second metacarpal shaft around to the dorsum 50 of hand 2. Like the sockets 10 and 310, special care is taken to limit excessive pressure around the radial fossa. See FIG. 1.

The second arced portion of socket 410 is configured like the second arced portion of socket 10.

Figure 11:
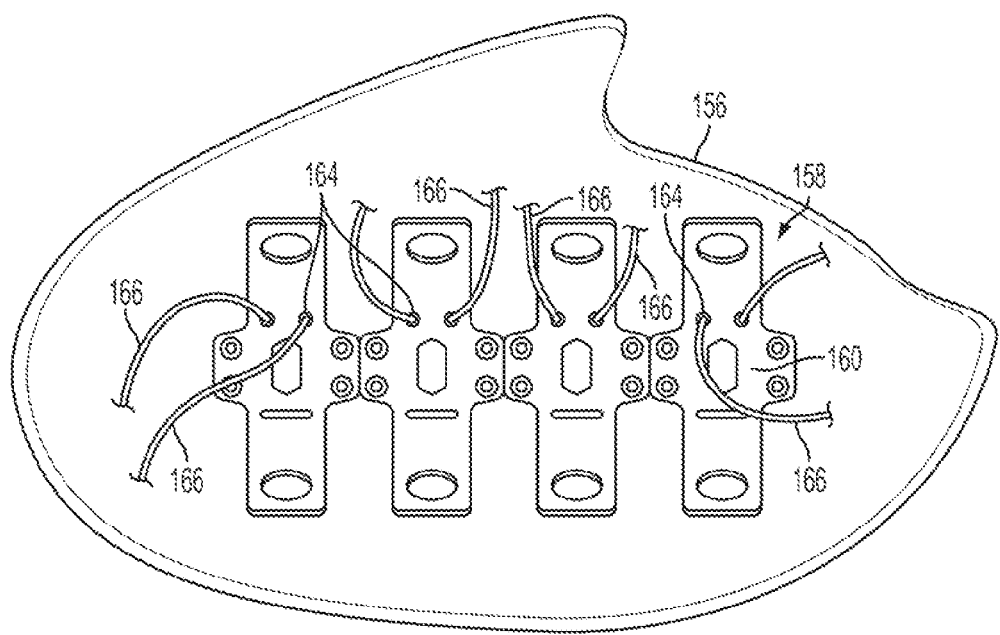
FIG. 11 is a view of the interior of the outer layer of an embodiment of a socket showing the fastener plate and wire ports.

There are a number of mechanisms by which the prosthetic members are releasably attached, such as screws, or attachment plates. As shown in FIG. 6-7, certain embodiments of the outer layer 70' include a distal end cap 156' joining at least a portion of the outer distal transverse dorsal band 150' and a portion of the outer distal transverse palmar band 76'. Referring to FIG. 11, a fastening mount 158 is positioned on the interior of the distal end cap 156 or 156' between the base layer 20 or 20' and the outer layer 70 or 70' for releasably attaching at least one prosthetic finger. The fastening mount 158 may be in the form of a plate 160 riveted, laminated, or otherwise fixedly attached in any suitable manner to the interior of the end cap 156. The prosthetic fingers may be attached through threaded posts on the back side, proximal ends of the fingers. The number of posts and attachment points will vary depending on the extent of the amputation or malformation of the hand and the number of prosthetic fingers to attach. There may be at least one and up to four attachment points on a fastening mount 158 on the distal cap 156 for releasably attaching at least one and up to four prosthetic fingers. If the prosthetic members include a tool for enabling the performance of an activity, the attachment point is typically on the palmar side of the socket by means of a quick disconnect mount. Any suitable know mount may be employed to releasably but securely mount a tool.

An exemplary fastening mount, plate 160 is shown in FIG. 11. Prosthetic fingers may be mounted in any suitable releasable locking engagement. It is beneficial to be able to remove the prosthetic members to allow replacement and repair.

Figure 12:
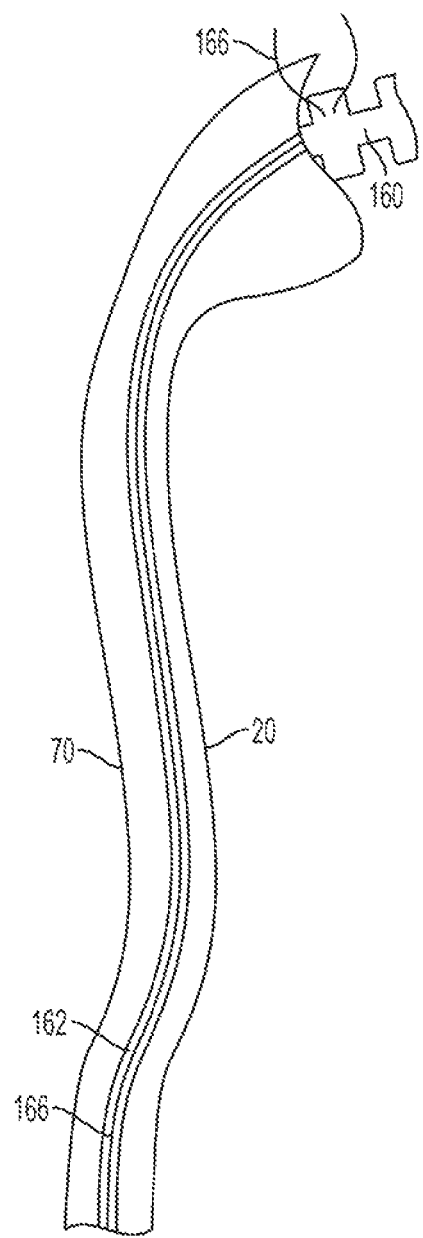
FIG. 12 is a section view of the base layer and outer layer with a channel formed between the two layers and a wire running through the channel to a port in a portion of the fastener plate.

In order to provide power for articulation of the prosthetic members, a plurality of channels 162 may be formed in one or both of the base layer 20 and the outer layer 70 for receiving signal transfer members, such as wires 166. The fastening mount 158 may have at least one port 164 in communication with at least one channel 162 for connecting the signal transfer members 166 to the at least one prosthetic member. As shown in FIG. 12, the plurality of channels 162 may be positioned between the base layer 20 and the outer layer 70. While the channels 162 are shown running in a distal to proximal direction, or curved generally in that direction, other suitable arrangements for connecting the signal transfer members to the prosthetic fingers or other prosthetic members may be used. The base layer 20 and the outer layer 70 may be releasably attached to each other by any suitable known means that will provide a secure but releasable connection, such as, for example, with screws, bolts, snaps, hooks, complementary lock and key arrangements, and the like 200. Alternatively, the base layer 20 and the outer layer 70 may be laminated together.

The partial hand anatomically contoured socket 10, 310, 410 may be formed by obtaining an impression of a patient's residual limb and creating a positive model of the patient's residual limb using suitable known procedures. Those skilled in the art will appreciate that the exact dimensions and contours of the socket depend on the nature and extent of the loss and the size and shape of the residual extremity. After the model is made, the novel specific and unique modifications to the positive model of the patient's residual limb are made to form the features described herein. Modifications may include accentuations of pressure, by removal of material from the positive model, along the palmar aspect of the shafts and necks s of the $3^{rd}$ and $4^{th}$ metacarpals, along the ulnar aspect of the shaft and neck of the $5^{th}$ metacarpal, and the radial aspect of the shaft and neck of the $4^{th}$ metacarpal. These specific modifications also serve to generally increase the overall pressure the base layer exerts on the residual anatomy thereby creating an expansion force through the fenestrated areas of the socket which enhances the overall stability, suspension, and proprioception of the socket The fabrication results in a thin yet strong socket 10, 310, 410. The thickness of the socket may range from 1/32 to 1/8 inch. When the anatomical criteria described herein are utilized for purposes of modification of the positive model, unique pressures and reliefs are created to allow for proper suspension of the socket, comfort, and enhanced range of motion.

The socket 10, 310, 410 may be formed from a polymer matrix composite, which may be selected from the group consisting of thermoplastic resins and thermoset resins. Any suitable known thermoplastic resins or thermoset resins may be used. Flexible or rigid thermoplastics and thermoset resins are useful. The material should provide a stable base of support. Too much flexibility degrades the efficacy of the socket design and its ability to suspend on the limb. The use of flexible thermoplastics is appropriate for a thin interface for comfort against the skin. In the embodiments where the socket is made of two pieces, a flexible base layer in the form of a socket interface and an outer layer or frame, the outer layer or frame must be rigid. The rigid layer must be made with a composite of a thermoset resin and carbon fiber or a pre-impregnated carbon fiber material. Two types of materials are used to achieve a high strength and rigidity but maintain an extremely thin frame, thus reducing the overall thickness and enhance cosmetics. Exemplary materials include epoxide polymers, such as EpoxyAcryl™ resins. However, numerous other examples are commercially available and will suffice. Fiber reinforced laminates and pre-impregnated composite materials, such as pre-impregnated carbon materials and carbon fiber products pre-impregnated with an epoxy resin, such as those available from Carbon Express, LLC may also be utilized to fabricate the frame of the design.

Fiber reinforced laminates can be made for example, in two ways; a "wet" layup or a pre-impregnated fiber layup. The "wet" laminate process can be used to create molded shapes from carbon fiber and resin. In the pre-impregnated fiber method, the fiber is pre-impregnated with resin and frozen to prevent the resin from curing prematurely. The resulting material is thawed and hand laid into a mold to the proper thickness and cured by one of two methods. The resin volume of the resulting laminate may be precisely controlled and is stiffer and stronger than a wet laminate of equivalent thickness.

The socket 10, 310, 410 is specifically designed to provide a stable, less intrusive or constrictive base on the amputated or missing portion of second through fifth digits at the metacarpals to provide a functional foundation for prosthetic fingers. All materials used that are in contact with a patient must be made of biocompatible materials.

Alternative techniques for obtaining the positive model can be utilized. For example, a three dimensional digital model from known scanning processes can be obtained using software aided modification of the digital model, and a computer aided model creation such as carving or 3D printing can create the positive model. Many 3D printing and modeling products suitable for use in forming a prostheses are available.

The enhanced stability and suspension achieved through the socket design described herein creates a firm foundation for placement of a variety of individualized prosthetic members. The embodiments of the socket 10, 310, 410 enable better use of independently articulating prosthetic finger components and/or other attachments for specific activities. This is an advantage over existing partial hand prosthetic fabricated sockets. Notwithstanding the foregoing, those skilled in the art will appreciate that nonarticulating prosthetic fingers may be attached to the socket 10, 310, 410.

An advantage of the design of the socket 10, 310, 410 over other forms of partial hand socket designs is the allowance of freedom to use the wrist in all ranges and planes. This freedom provides the partial hand amputation patient with complete functional use of the wrist and forearm while utilizing a functional prosthesis.

Although the various embodiments of the devices have been described herein in connection with certain disclosed embodiments, many modifications and variations to those embodiments may be implemented. For example, different types of finger prostheses and connectors for special use equipment or tools may be used. Also, where materials are disclosed for certain components, other materials may be used. The foregoing description and following claims are intended to cover all such modification and variations.

What is claimed is:

1. A socket for use with a partial prosthesis of the hand, wherein the natural hand has an ulnar side and a radial side and retains thenar and hypo-thenar eminences, at least the body portions of the metacarpals, and at least a portion of the proximal phalanx of the thumb, the socket comprising:

a contoured base layer having a palmar portion, a dorsal portion, a first arced portion joining the palmar and dorsal portions on the ulnar side, and a second arced portion joining the palmar and dorsal portions on the radial side, the palmar portion comprising:
a transverse distal band having a first section and a second section and being positioned in use proximate to the transverse metacarpal arch of a natural hand,
an axial band having a distal end and a proximal end, the distal end being joined to the transverse distal band, and
a transverse proximal band joined to the proximal end of the axial band and extending laterally therefrom in one direction in a position opposite the first section of the transverse distal band, the transverse proximal band configured for positioning in use along a portion of the proximal transverse arch of the carpal rows distal to the wrist crease of the natural hand,
the first section of the transverse distal band, the axial band, and the transverse proximal band defining an opening configured in use to expose the hypo-thenar eminence of the natural hand, and the second section of the transverse distal band and the axial band defining a perimeter of an open area configured in use to expose the thenar eminence and radial side of the wrist of the natural hand;

the dorsal portion comprising:
a transverse dorsal band contoured to span, in use, a mid-portion of the dorsum of the natural hand in an area initiating distal to the dorsal side of the wrist crease, the dorsal band having a first end and a second end;

the first arced portion joined to the first end of the transverse dorsal band, the first section of the transverse distal band, and the transverse proximal band and defining a perimeter of the hypo-thenar opening; and, the second arced portion joined to the second end of the transverse dorsal band and the second section of the transverse distal band;

a dorsal axial band that is joined to and extending proximally from the second end of the transverse dorsal band;

said socket configured to define the open area from the perimeter of the thenar eminence to the dorsal axial band.

2. The socket recited in claim 1 wherein the dorsal axial band has a terminal portion positioned in use at a location distal to the wrist crease of the natural hand.

3. The socket recited in claim 2 wherein the terminal portion of the dorsal axial band is contoured to conform to the natural hand sufficiently to touch the natural hand, in use, and to avoid compression of the radial fossa.

4. The socket recited in claim 1 wherein the axial band of the palmar portion is contoured to touch, in use, the palm of the natural hand along a position between the thenar and hypo-thenar eminences.

5. The socket recited in claim 1 wherein the first and second arced portions and the transverse distal and transverse dorsal bands are contoured to provide, in use, stabilizing pressure proximate the transverse metacarpal arch of a natural hand.

6. The socket recited in claim 1 wherein the axial band of the palmar portion, the transverse proximal band, and the first arced portion are contoured to provide, in use, stabilizing pressure along a location distal to the wrist crease of the natural hand and to avoid compression of the pisiform bone area of the natural hand.

7. The socket recited in claim 1 further comprising an outer layer joined to the base layer, the outer layer configured and contoured to substantially match the configuration and contours of the base layer.

8. The socket recited in claim 7 wherein the base layer and the outer layer are releasably attached to each other.

9. The socket recited in claim 7 wherein the base layer and the outer layer are laminated together.

10. The socket recited in claim 1 further comprising a distal end cap joining at least a portion of the distal transverse dorsal band and a portion of the distal transverse palmar band.

11. The socket recited in claim 10 further comprising a fastening mount on the distal end cap for releasably attaching at least one prosthetic member.

12. The socket recited in claim 11 wherein the prosthetic member is a prosthetic finger.

13. The socket recited in claim 12 wherein there are from one to four prosthetic fingers mounted on the fastening mount.

14. The socket recited in claim 12 further comprising a plurality of channels formed in one or both of the base layer and the outer layer for receiving signal transfer members.

15. The socket recited in claim 14 wherein the fastening mount has at least one port in communication with at least one channel for connecting the signal transfer members to the at least one prosthetic member.

16. The socket recited in claim 12 further comprising a plurality of channels positioned between the base layer and the outer layer for receiving signal transfer members.

17. The socket recited in claim 1 further comprising a fastening mount on the palmar portion for releasably lockingly mounting a prosthetic member comprising a tool for enabling the performance of an activity.

18. A socket for use with a partial prosthesis of the hand, wherein the natural hand has an ulnar side and a radial side and retains thenar and hypo-thenar eminences, at least the body portions of the metacarpals, and at least a portion of the proximal phalanx of the thumb, the socket comprising:

a base layer molded to encapsulate and conform to the contours of a natural hand, the base layer having a dorsal portion and a palmar portion, the palmar portion having a distal edge positioned, in use, proximate to the transverse metacarpal arch of a natural hand, and the dorsal portion having a distal edge positioned, in use, to span a mid-portion of the dorsum of the natural hand in an area proximal to the area of the second through fifth metacarpal heads of a natural hand, the palmar portion of the base layer defining a first open area around the hypo-thenar eminence and a second open area surrounding the thenar eminence on the palmar portion and extending around the radial side to the second metacarpal on the dorsal portion, and the palmar and dorsal portions having proximal edges positioned, in use, distal to the wrist crease to permit, in use, unhindered motion of the wrist;

said socket further comprising:

a first arced portion joining the palmar and dorsal portions on the ulnar side, and a second arced portion joining the palmar and dorsal portions on the radial side, the palmar portion comprising:

a transverse distal band having a first section and a second section and being positioned in use proximate to the transverse metacarpal arch of a natural hand, an axial band having a distal end and a proximal end, the distal end being joined to the transverse distal band, and a transverse proximal band joined to the proximal end of the axial band and extending laterally therefrom in one direction in a position opposite the first section of the transverse distal band, the transverse proximal band configured for positioning in use proximate to a portion of the proximal transverse arch of the carpal rows distal to the wrist crease of the natural hand;

the dorsal portion comprising:

a transverse dorsal band contoured in use to span a mid-portion of the dorsum of the natural hand in an area initiating distal to the dorsal side of the wrist crease, the dorsal band having a first end and a second end, and a dorsal axial band joined to and extending proximally from the second end of the transverse dorsal band, perimeter of the thenar eminence to the dorsal axial band;

the first arced portion being joined to the first end of the transverse dorsal band;

the second arced portion being joined to the second end of the transverse dorsal band and the second section of the transverse distal band; and, the first section of the transverse distal band, the axial band, the transverse proximal band, and the first arced portion defining the first open area, and the second section of the transverse distal band, the axial band of the palmar portion, and the radial side of the dorsal axial band defining the second open area.

19. The socket recited in claim 18 further comprising an outer layer joined to the base layer, the outer layer configured and contoured to substantially match the configuration and contours of the base layer.

20. The socket recited in claim 19 further comprising a distal end cap having a fastening mount embedded therein for releasably attaching at least one prosthetic member.

21. The socket recited in claim 20 further comprising a plurality of channels formed in one or both of the base layer and the outer layer for receiving signal transfer members, and each fastening mount having at least one port in communication with at least one channel for connecting the signal transfer members to the at least one prosthetic member.

\* \* \* \* \*